(12) United States Patent
Old (10) Patent No.: US 7,547,685 B2
(45) Date of Patent: Jun. 16, 2009

(54) THERAPEUTIC SUBSTITUTED PYRROLIDONE COMPOUNDS

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 62 days.

(21) Appl. No.: 11/577,870

(22) PCT Filed: Nov. 7, 2005

(86) PCT No.: PCT/US2005/040298

§ 371 (c)(1),
(2), (4) Date: Apr. 24, 2007

(87) PCT Pub. No.: WO2006/052893

PCT Pub. Date: May 18, 2006

(65) Prior Publication Data

US 2008/0015239 A1    Jan. 17, 2008

Related U.S. Application Data

(60) Provisional application No. 60/629,651, filed on Nov. 19, 2004, provisional application No. 60/626,294, filed on Nov. 8, 2004.

(51) Int. Cl.
| | |
|---|---|
| *A61K 31/675* | (2006.01) |
| *A61K 31/4015* | (2006.01) |
| *C07D 257/04* | (2006.01) |
| *C07D 409/06* | (2006.01) |
| *C07F 9/38* | (2006.01) |

(52) U.S. Cl. .................. 514/91; 514/382; 514/422; 514/424; 548/252; 548/413; 548/525; 548/527

(58) Field of Classification Search .......... 514/381, 514/422, 424, 382, 91; 548/252, 527, 551, 548/517, 543, 413, 525
See application file for complete search history.

(56) References Cited

U.S. PATENT DOCUMENTS

| 6,552,067 | B2 | 4/2003 | Cameron et al. |
| 6,586,468 | B1 | 7/2003 | Maruyama et al. |
| 7,402,605 | B2 * | 7/2008 | Tani et al. ............ 514/424 |
| 2003/0207925 | A1 | 11/2003 | Cameron et al. |
| 2008/0132543 | A1 * | 6/2008 | Im et al. ............ 514/327 |

FOREIGN PATENT DOCUMENTS

| WO | WO03/053923 | 7/2003 |
| WO | WO03/074483 | 9/2003 |
| WO | WO03/077910 | 9/2003 |
| WO | WO03/103664 | 12/2003 |
| WO | WO2004/019938 | 3/2004 |
| WO | WO2004/037786 | 5/2004 |
| WO | WO2004/078103 | 9/2004 |

OTHER PUBLICATIONS

Wolff et al., Burger's Medicinal Chemistry and Drug Discovery, 1994, Wiley-Interscience, Fifth Edition, vol. I: Principles and Practice, pp. 975-977.*

* cited by examiner

*Primary Examiner*—Kamal A Saeed
*Assistant Examiner*—Kristin Bianchi
(74) *Attorney, Agent, or Firm*—Allergan, Inc.; Kevin Forrestal (57) ABSTRACT

Compounds comprising

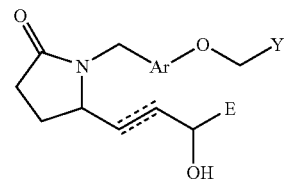

or a pharmaceutically acceptable salt or a prodrug thereof are disclosed herein. Details are provided herein. Compositions, methods, and medicaments related thereto are also disclosed.

19 Claims, 1 Drawing Sheet

Fig. 1

THERAPEUTIC SUBSTITUTED PYRROLIDONE COMPOUNDS

CROSS REFERENCE TO RELATED APPLICATIONS

This is a PCT application which claims the benefit of Provisional Application No. 60/626,294 filed Nov. 8, 2004 and Provisional Application No. 60/629,651 filed Nov. 19, 2004, incorporated in their entirety herein.

DESCRIPTION OF RELATED ART

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

WO04065365 discloses compounds such as the ones shown below.

WO04037813 discloses compounds such as the one shown below.

WO03103604 discloses compounds such as the one shown below.

United States Patent Application Publication No. 2003012009 and WO03008377 disclose compounds such as the one shown below.

U.S. Pat. No. 6,747,054 discloses compounds such as the one shown below.

U.S. Pat. No. 6,552,067 discloses compounds such as the one shown below, where X is methylene or O, and Z is —(CH$_2$)$_3$—, thienyl, thiazolyl, or phenyl.

WO04078103 discloses compounds such as the one shown below.

Other related compounds are disclosed in the following documents: WO04037786, WO04019938, WO03103664, WO03077910, WO03074483, WO03053923, WO03009872, and United States Patent Application Publication No. 20030207925.

Inflammatory bowel disease (IBD) is a group of disease characterized by inflammation in the large or small intestines and is manifest in symptoms such as diarrhea, pain, and weight loss. Nonsteroidal anti-inflammatory drugs have been shown to be associated with the risk of developing IBD, and recently Kabashima and colleagues have disclosed that "EP4 works to keep mucosal integrity, to suppress the innate immunity, and to downregulate the proliferation and activation of CD4+ T cells. These findings have not only elucidated the mechanisms of IBD by NSAIDs, but also indicated the therapeutic potential of EP4-selective agonists in prevention and treatment of IBD." (Kabashima, et. al., The Journal of Clinical Investigation, April 2002, Vol. 9, 883-893)

Prostaglandin EP$_4$ selective agonists are believed to have several other medical uses. For example, U.S. Pat. No. 6,552,067 B2 teaches the use of prostaglandin EP4 selective agonists for the treatment of "methods of treating conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth in a mammal".

U.S. Pat. No. 6,586,468 B1 teaches that prostaglandin EP4 selective agonists "are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burn, systemic granuloma, ulcerative colititis, Crohn's diseases, hypercytokinemia at dialysis, multiple organ failure, shock, etc. They are also connected with sleeping disorders and platelet coagulations, and therefore they are thought to be useful for these diseases."

DESCRIPTION OF THE INVENTION

Compounds comprising or a pharmaceutically acceptable salt or a prodrug thereof are disclosed herein;

wherein a dashed line represents the presence or absence of a bond;

Y is an organic acid functional group, or an amide or ester thereof comprising from 0 to 12 carbon atoms;

or Y is hydroxymethyl or an ether thereof comprising from 0 to 12 carbon atoms; or Y is a tetrazolyl functional group;

Ar is interarylene or interheteroarylene; and

E is hydrocarbyl or heterohydrocarbyl.

Compounds having the stereochemistry shown in the structures below are specifically contemplated herein.

Pharmaceutically acceptable salts or prodrugs of compounds of these structures are also contemplated.

In the structures disclosed herein, a dashed line represents the presence of absence of a bond. Thus, compounds according to the structures shown below are contemplated.

Pharmaceutically acceptable salts or prodrugs of compounds of these structures are also contemplated.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substitutuents in addition to the two parts of the molecule it connects.

In one embodiment, Ar is substituted or unsubstituted interphenylene, interthienylene, interfurylene, or interpyridinylene. In another embodiment Ar is interphenylene, interthienylene, or interfurylene. In another embodiment Ar is interphenylene (Ph).

In one embodiment Ar is 1,3-substituted, i.e. the attachment occurs at positions on the ring having one ring atom in between them. Meta-interphenylene such as when A has the structure shown below, are examples.

Other examples for include the structures shown below.

Substituents for interarylene or heterointerarylene are the same as those for aryl or heteroaryl, and will described in detail later herein.

An organic acid functional group is an acidic functional group on an organic molecule. While not intending to be limiting, organic acid functional groups generally comprise an oxide of carbon, sulfur, or phosphorous. Thus, while not intending to limit the scope of the invention in any way, in certain compounds Y is a carboxylic acid, sulfonic acid, or phosphonic acid functional group, i.e. one of the structures shown below.

Salts of any of these acids of any pharmaceutically acceptable form are also contemplated.

Additionally, an amide or ester of one of the organic acids shown above comprising from 0 to 12 carbon atoms is also contemplated. In an ester, a hydrocarbyl moiety replaces a hydrogen atom of an acid such as in a carboxylic acid ester, e.g. $CO_2R^2$. In an amide, an amine group replaces an OH of the acid. An amine is a moiety with a central nitrogen that has exactly three bonds to C or H. Examples of amides include $CON(R^2)_2$, $CON(OR^2)R^2$, $CON(CH_2CH_2OH)_2$, and $CONH(CH_2CH_2OH)$. Moieties such as $CONHSO_2R^2$ are also amides of the carboxylic acid notwithstanding the fact that they may also be considered to be amides of the sulfonic acid $R^2$—$SO_3H$.

While not intending to limit the scope of the invention in any way, Y may also be hydroxymethyl or an ether thereof comprising from 0 to 12 carbon atoms. Thus, compounds having a structure shown below are possible.

Additionally, ethers of these compounds are also possible. An ether is defined as a functional group wherein a hydrogen of an hydroxyl is replaced by carbon, e.g., Y is $CH_2OCH_3$, $CH_2OCH_2CH_3$, etc.

Finally, while not intending to limit the scope of the invention in any way, Y may be a tetrazolyl functional group, i.e. compounds having a structure such as one of those shown below.

When $R^2$ is hydrogen, the tetrazolyl functional group has two tautomeric forms, which can rapidly interconvert in aqueous or biological media, and are thus equivalent to one another. These tautomers are shown below.

Additionally, if $R^2$ is $C_1$-$C_6$ alkyl, phenyl, or biphenyl, other isomeric forms of the tetrazolyl functional group such as the one shown below are also possible, all of these are considered to be within the scope of the term "tetrazolyl".

While not intending to limit the scope of the invention in any way, in one embodiment, Y is selected from the group consisting of $CO_2(R^2)$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$, and tetrazolyl-$R^2$; wherein $R^2$ is independently H, $C_1$-$C_6$ alkyl, phenyl, or biphenyl.

E is hydrocarbyl or heterohydrocarbyl.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:
linear alkyl such as methyl, ethyl, propyl, n-butyl, n-pentyl, n-hexyl, and the like;
branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;
cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.
Alkenyl is hydrocarbyl having one or more double bonds including linear alkenyl, branched alkenyl, cyclic alkenyl, and combinations thereof in analogy to alkyl.
Alkynyl is hydrocarbyl having one or more triple bonds including linear alkynyl, branched alkynyl, cyclic alkynyl and combinations thereof in analogy to alkyl.
Aryl is an unsubstituted or substituted aromatic ring or ring system such as phenyl, naphthyl, biphenyl, and the like. Aryl may or may not be hydrocarbyl, depending upon whether it has substituents with heteroatoms.
Arylalkyl is alkyl which is substituted with aryl. In other words alkyl connects aryl to the remaining part of the molecule. Examples are —$CH_2$-Phenyl, —$CH_2$—$CH_2$-Phenyl, and the like. Arylalkyl may or may not be hydrocarbyl, depending upon whether it has substituents with heteroatoms.

Unconjugated dienes or polyenes have one or more double bonds which are not conjugated. They may be linear, branched, or cyclic, or a combination thereof.

Combinations of the above are also possible.

For the compounds disclosed herein, hydrocarbyl having no ring has 12 or fewer carbon atoms, and hydrocarbyl having one or more rings has 18 or fewer carbon atoms.

Heterohydrocarbyl is a moiety comprising heteroalkyl, heteroaryl, or heteroatom substituted aryl, or a combination thereof, either alone or in combination with hydrocarbyl and/or aryl. The following moieties are typical examples.

Heteroalkyl is alkyl having one or more carbon atoms substituted with O or S atoms, provided that no carbon has more than 1 covalent bond to O or S, i.e. there are no C=O, —O—$CH_2$—O—, —S—$CH_2$—S—, etc.; and that O and S are only bonded to carbon, i.e. there are no OH, SH, $SO_3H$, etc.

Heteroatom substituted aryl comprises one or more substituents on the aryl ring or ring system, said substituents comprising one or more atoms which are not H or C.

Heteroatom substituted arylalkyl comprises one or more substituents on the aryl ring or ring system, said substituents comprising one or more atoms which are not H or C.

Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

Heteroarylalkyl is alkyl which is substituted with heteroaryl. In other words alkyl connects heteroaryl to the remaining part of the molecule. Examples are —$CH_2$-thienyl, —$CH_2CH_2$-benzothienyl, and the like.

Heteroarylheteroalkyl is heteroalkyl which is substituted with heteroaryl. In other words heteroalkyl connects heteroaryl to the remaining part of the molecule. Examples are —$CH_2$O-thienyl, —$CH_2$S-benzothienyl, and the like.

Arylheteroalkyl is heteroalkyl which is substituted with aryl. In other words heteroalkyl connects aryl to the remaining part of the molecule. Examples are —CH$_2$O-phenyl, —CH$_2$S-naphthyl, and the like.

The substituents of aryl or heteroaryl may have up to 12 non-hydrogen atoms each and as many hydrogen atoms as necessary. Thus, while not intending to limit the scope of the invention in any way, the substituents may be:

hydrocarbyl, such as alkyl, alkenyl, alkynyl, and the like, and combinations thereof;
hydrocarbyloxy, meaning O-hydrocarbyl such as OCH$_3$, OCH$_2$CH$_3$, O-cyclohexyl, etc, up to 11 carbon atoms;
hydroxyhydrocarbyl, meaning hydrocarbyl-OH such as CH$_2$OH, C(CH$_3$)$_2$OH, etc, up to 11 carbon atoms;
nitrogen substituents such as NO$_2$, CN, and the like, including amino, such as NH$_2$, NH(CH$_2$CH$_3$OH), NHCH$_3$, and the like up to 11 carbon atoms;
carbonyl substituents, such as CO$_2$H, ester, amide, and the like;
halogen, such as chloro, fluoro, bromo, and the like
fluorocarbyl, such as CF$_3$, CF$_2$CF$_3$, etc.;
phosphorous substituents, such as PO$_3^{2-}$, and the like;
sulfur substituents, including S-hydrocarbyl, SH, SO$_3$H, SO$_2$-hydrocarbyl, SO$_3$-hydrocarbyl, and the like.

In certain embodiments, the number of non-hydrogen atoms is 6 or less in a substituent. In other embodiments, the number of non-hydrogen atoms is 3 or less in a substituent. In other embodiments, the number of non-hydrogen atoms on a substituent is 1.

In certain embodiments, the substituents contain only hydrogen, carbon, oxygen, halo, nitrogen, and sulfur. In other embodiments, the substituents contain only hydrogen, carbon, oxygen, and halo.

Unless otherwise indicated, references to aryl, heteroaryl, phenyl, thienyl, benzothienyl, and the like are intended to mean both the substituted and the unsubstituted moiety.

For the compounds disclosed herein, heterohydrocarbyl having no ring has 12 or fewer carbon atoms, and heterohydrocarbyl having one or more rings has 18 or fewer carbon atoms.

Thus embodiments wherein E is any of the hydrocarbyl or heterohydrocarbyl moieties disclosed herein are contemplated.

In certain embodiments, E is hydrocarbyl having from 1 to 12 carbon atoms. In other embodiments, E is hydrocarbyl having from 1 to 6 carbon atoms. In other embodiments, E is n-pentyl.

In one embodiment E is X-aryl or X-heteroaryl, wherein X is a covalent bond, CH$_2$, CH$_2$CH$_2$, CH$_2$O, or CH$_2$S.

In another embodiment E is X-aryl or X-heteroaryl having from 0 to 2 substituents, wherein aryl or heteroaryl is monocyclic or bicyclic, and said substituents have up to 6 non-hydrogen atoms each; said non-hydrogen atoms being selected from the group consisting of carbon, oxygen, sulfur, nitrogen, fluorine, chlorine, and bromine.

In another embodiment E is X-phenyl, X-napthyl, X-thienyl, X-benzothienyl, X-furyl, or X-benzofuryl, which may have up to 2 substituents selected from the group consisting or F, Cl, Br, Me, OMe, and CF$_3$; and wherein X is CH$_2$ or a covalent bond.

In another embodiment E is CH$_2$CH$_2$-(2-thienyl), CH$_2$CH$_2$-(3-thienyl), CH$_2$-(2-thienyl), CH$_2$-(3-thienyl), CH$_2$CH$_2$-(2-(3-chlorobenzothienyl)), CH$_2$CH$_2$-(3-benzothienyl), CH$_2$-(2-(3-chlorobenzothienyl)), or CH$_2$-(3-benzothienyl).

Another embodiment comprises or a pharmaceutically acceptable salt or a prodrug thereof; wherein B is aryl or heteroaryl.

Another compound comprises or a pharmaceutically acceptable salt or a prodrug thereof.

In another embodiment, B is substituted or unsubstituted phenyl, napthyl, thienyl, benzothienyl, furyl, or benzofuryl.

Another compound comprises or a pharmaceutically acceptable salt or a prodrug thereof; wherein n is 0 or 1; and
R$^1$ is hydrogen, fluoro, chloro, bromo, methyl, methoxy, or CF$_3$

Another compound comprises or or a pharmaceutically acceptable salt or a prodrug thereof;
wherein n is 0 or 1; and
R¹ is hydrogen, fluoro, chloro, bromo, methyl, methoxy, or CF₃.

Another compound comprises or a pharmaceutically acceptable salt or a prodrug thereof;
wherein R¹ is H or Cl.

Another compound comprises or a pharmaceutically acceptable salt or a prodrug thereof;
wherein R¹ is H or Cl.

Other compounds of interest are shown below.

Pharmaceutically acceptable salts and prodrugs of these compounds are also contemplated.

While not intending to limit the scope of the invention in any way, it is believed that the compound disclosed herein will be selective prostaglandin $EP_4$ agonists.

The compounds disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_4$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid humans in clinical trials for the treatment of irritable bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, markets pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

Synthetic Procedures

Figure 1:
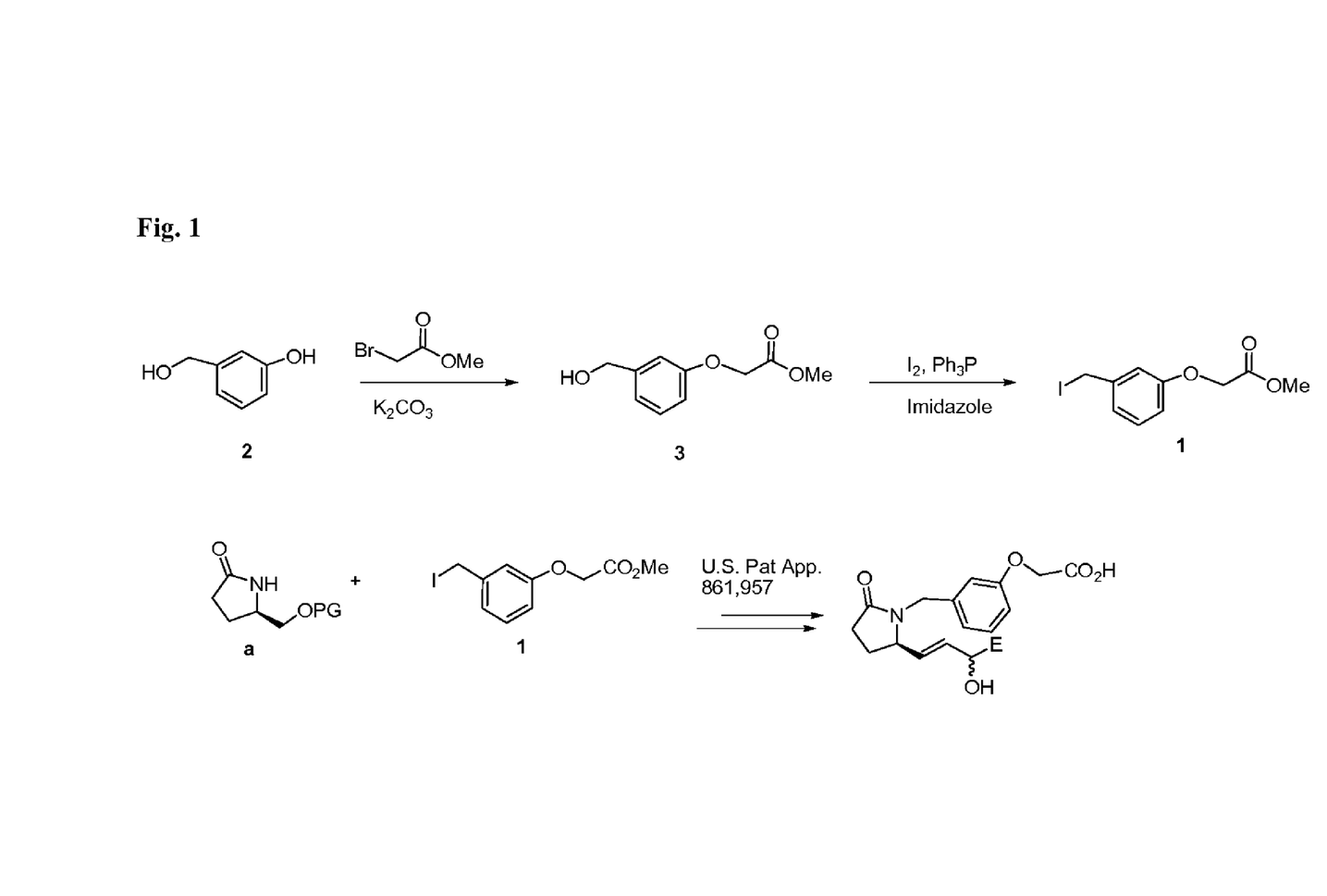
FIG. 1 depicts an exemplary synthetic route to the compounds of the invention.

The compounds disclosed herein may be prepared by an analogous procedure to that disclosed in U.S. patent application Ser. No. 861,957, filed on Jun. 3, 2004 (Example 50, starting p. 81, line 12), which is expressly incorporated by reference herein. In this procedure, compound 1 is substituted for ((Z)-4-chloro-but-2-enyloxy)-acetic acid ethyl ester (p. 82, line 11) and compound a is substituted for (R)-6-(1-Ethoxyethoxymethyl)-piperidin-2-one ethyl vinyl ether, and the remainder of the procedure is carried out as described. Compound 1 may be prepared as disclosed in FIG. 1 by etherification of 3-hydroxymethylphenol (compound 2) with bromoacetic acid methyl ester in the presence of carbonate base to form compound 3, which is worked up and purified according to standard procedures. Compound 3 is treated with iodine, triphenylphosphine, and imidazole, and worked up and purified using standard procedures to obtain compound 1. A procedure for preparing compound 1 is also disclosed in DE3601248.

Biological Activity

The activity of compounds disclosed herein is tested according to the following procedures.

17

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors are washed with TME buffer, scraped from the bottom of the flasks, and homogenized for 30 sec using a Brinkman PT 10/35 polytron. TME buffer is added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate is centrifuged at 19000 r.p.m. for 20 min at 4° C. using a Beckman Ti-60 rotor. The resultant pellet is resuspended in TME buffer to give a final 1 mg/ml protein concentration, as determined by Biorad assay. Radioligand binding competition assays vs. [$^3$H-]17-phenyl $PGF_{2\alpha}$ (5 nM) are performed in a 100 µl volume for 60 min. Binding reactions are started by adding plasma membrane fraction. The reaction is terminated by the addition of 4 ml ice-cold TRIS-HCl buffer and rapid filtration through glass fiber GF/B filters using a Brandel cell harvester. The filters are washed 3 times with ice-cold buffer and oven dried for one hour. Non-specific binding is determined with 10 uM unlabeled 17-phenyl $PGF_{2\alpha}$.

[$^3$H—] $PGE_2$ (5 nM; specific activity 180 Ci mmol) is used as the radioligand for EP receptors. Binding studies employing $EP_1$, $EP_2$, $EP_3$, $EP_4$ are performed in duplicate in at least three separate experiments. A 200 µl assay volume is used. Incubations are for 60 min at 25° C. and are terminated by the addition of 4 ml of ice-cold 50 mM TRIS-HCl, followed by rapid filtration through Whatman GF/B filters and three additional 4 ml washes in a cell harvester (Brandel). Non-specific binding is determined with $10^{-5}$ M of unlabeled $PGE_2$.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), are cultured in 100 mm culture dishes in high-glucose DMEM medium containing 10% fetal bovine serum, 2 mM 1-glutamine, 250 µg/ml geneticin (G418) and 200 µg/ml hygromycin B as selection markers, and 100 units/ml penicillin G, 100 µg/ml streptomycin and 0.25 µg/ml amphotericin B.

b) Calcium Signal Studies on the FLIPR™

Cells are seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells are then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates are washed four times with HBSS-HEPES buffer to remove excess dye leaving 100 µl in each well. Plates are re-equilibrated to 37° C. for a few minutes.

Cells are excited with an Argon laser at 488 nm, and emission is measured through a 510-570 nm bandwidth emission filter (FLIPR™, Molecular Devices, Sunnyvale, Calif.). Drug solution is added in a 50 µl volume to each well to give the desired final concentration. The peak increase in fluorescence intensity is recorded for each well. On each plate, four wells each serve as negative (HBSS-HEPES buffer) and positive controls (standard agonists: BW245C (hDP); $PGE_2$ ($HEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well is then expressed relative to the controls.

Compounds are tested in a high-throughput (HTS) or concentration-response (CoRe) format. In the HTS format, forty-four compounds per plate are examined in duplicates at a concentration of $10^{-5}$ M. To generate concentration-response curves, four compounds per plate are tested in duplicates in a concentration range between $10^{-5}$ and $10^{-11}$ M. The duplicate values are averaged. In either, HTS or CoRe format each compound is tested on at least 3 separate plates using cells from different passages to give an $n \geqq 3$.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound having the structure:

or a pharmaceutically acceptable salt thereof;
wherein a dashed line represents the presence or absence of a bond;
Y is an organic acid functional group, or an amide or ester thereof comprising from 0 to 12 carbon atoms; or Y is hydroxymethyl or an ether thereof comprising from 0 to 12 carbon atoms; or Y is a tetrazolyl functional group;
Ar is interarylene or interheteroarylene; and
B is X-aryl or X-heteroaryl, wherein X is a covalent bond, $CH_2$, $CH_2CH_2$, $CH_2O$, or $CH_2S$.

2. The compound of claim 1 wherein the interarylene or interheteroarylene bears 1,3-ring substitution.

3. The compound of claim 1 wherein Ar is interphenylene, interthienylene, or interfurylene.

4. The compound of claim 3 wherein Ar is 1,3-interphenylene.

5. The compound of claim 1 wherein B is X-phenyl, X-napthyl, X-thienyl, X-benzothienyl, X-furyl, or X-benzofuryl, which may have up to 2 substituents selected from the group consisting or F, Cl, Br, Me, OMe, and $CF_3$; and wherein X is $CH_2$ or a covalent bond.

6. The compound of claim 5 wherein B is $CH_2CH_2$-(2-thienyl), $CH_2CH_2$-(3-thienyl), $CH_2$-(2-thienyl), $CH_2$-(3-thienyl), CH₂CH₂-(2-(3-chlorobenzothienyl)), CH₂CH₂-(3-benzothienyl), CH₂-(2-(3-chlorobenzothienyl)), or CH₂-(3-benzothienyl)).

7. The compound of claim 1 wherein Ar is interphenylene.
8. The compound of claim 1 represented by the formula or a pharmaceutically acceptable salt thereof;
wherein B is aryl or heteroaryl.
9. The compound of claim 8 wherein B is substituted or unsubstituted phenyl, napthyl, thienyl, benzothienyl, furyl, or benzofuryl.
10. The compound of claim 1 represented by the formula or a pharmaceutically acceptable salt thereof, wherein B is aryl or heteroaryl.
11. The compound of claim 10 wherein B is substituted or unsubstituted phenyl, napthyl, thienyl, benzothienyl, furyl, or benzofuryl.
12. The compound of claim 5 represented by the formula or a pharmaceutically acceptable salt thereof;
wherein n is 0 or 1; and
R¹ is hydrogen, fluoro, chloro, bromo, methyl, methoxy, or CF₃.

13. The compound of claim 12 represented by the formula or a pharmaceutically acceptable salt thereof;
wherein R¹ is H or Cl.
14. The compound of claim 12 represented by the formula or a pharmaceutically acceptable salt thereof;
wherein R¹ is H or Cl.
15. The compound of claim 1 wherein Y is selected from the group consisting of CO₂R, CONR₂, CON(OR)R, CON(CH₂CH₂OH)₂, CONH(CH₂CH₂OH), CH₂OH, P(O)(OH)₂, CONHSO₂R, SO₂NR₂, SO₂NHR, and tetrazolyl-R; wherein R is independently H, C₁-C₆ alkyl, phenyl, or biphenyl.
16. A method comprising administering an effective amount of a therapeutic agent to a mammal for one or more therapeutic purposes chosen from the treatment of glaucoma or ocular hypertension, the treatment of an irritable bowel disease, the maintenance of colonic mucous, or a combination thereof; said therapeutic agent comprising a compound of the formula a pharmaceutically acceptable salt of said compound or a combination thereof;
wherein a dashed line represents the presence or absence of a bond;
Y is an organic acid functional group, or an amide or ester thereof having from 0 to 12 carbon atoms; or Y is hydroxymethyl or an ether thereof having from 0 to 12 carbon atoms; or Y is a tetrazolyl functional group;
Ar is interarylene or interheteroarylene; and
B is aryl or heteroaryl.
17. The method of claim 16 wherein said therapeutic purpose is the treatment of glaucoma or ocular hypertension.
18. The method of claim 16 wherein said therapeutic purpose is the treatment of an irritable bowel disease.

19. A composition comprising a compound, said composition being an aqueous liquid which is formulated for topical ophthalmic administration, said compound represented by the formula or a pharmaceutically acceptable salt thereof;

wherein a dashed line represents the presence or absence of a bond;

Y is an organic acid functional group, or an amide or ester thereof having from 0 to 12 carbon atoms; or Y is hydroxymethyl or an ether thereof having from 0 to 12 carbon atoms; or Y is a tetrazolyl functional group;

Ar is interarylene or interheteroarylene; and

B is aryl or heteroaryl.

* * * * *